United States Patent [19]

Pawelletz et al.

[11] 4,144,494

[45] Mar. 13, 1979

[54] METHOD OF MAGNETICALLY TESTING TUBES DURING WELDING WHEREIN THE SAME MAGNETIC FIELD IS USED BOTH FOR HEATING AND TESTING

[75] Inventors: Reinhard Pawelletz; Heinz Schneider, both of Düsseldorf, Fed. Rep. of Germany

[73] Assignee: Mannesmann Aktiengesellschaft, Dusseldorf, Fed. Rep. of Germany

[21] Appl. No.: 832,618

[22] Filed: Sep. 12, 1977

[30] Foreign Application Priority Data

Sep. 10, 1976 [DE] Fed. Rep. of Germany ....... 2641367

[51] Int. Cl.$^2$ ............................................ G01R 33/12
[52] U.S. Cl. .................................. 324/220; 324/226; 324/240; 228/104
[58] Field of Search ............... 324/219, 220, 226, 228, 324/237–242; 228/103, 104

[56] References Cited

U.S. PATENT DOCUMENTS

| 1,978,252 | 10/1934 | Drake | 324/241 |
| 2,719,953 | 10/1955 | Waldie | 324/242 |
| 3,619,769 | 11/1971 | Kusenberger | 324/226 |

Primary Examiner—Robert J. Corcoran
Attorney, Agent, or Firm—Smyth, Pavitt, Siegemund, Jones & Martella

[57] ABSTRACT

In electromagnetic testing method for tubes is disclosed, which is used during continuous production of tubing from strip being formed into a tube followed by welding the adjoining edges. A magnetic field is applied from the outside, possibly being a field accompanying the welding process, and a pickup transducer is inserted from the tube forming location to scan the interaction of the penetrating field with the tube particularly the seam and adjacent zones.

1 Claim, 2 Drawing Figures

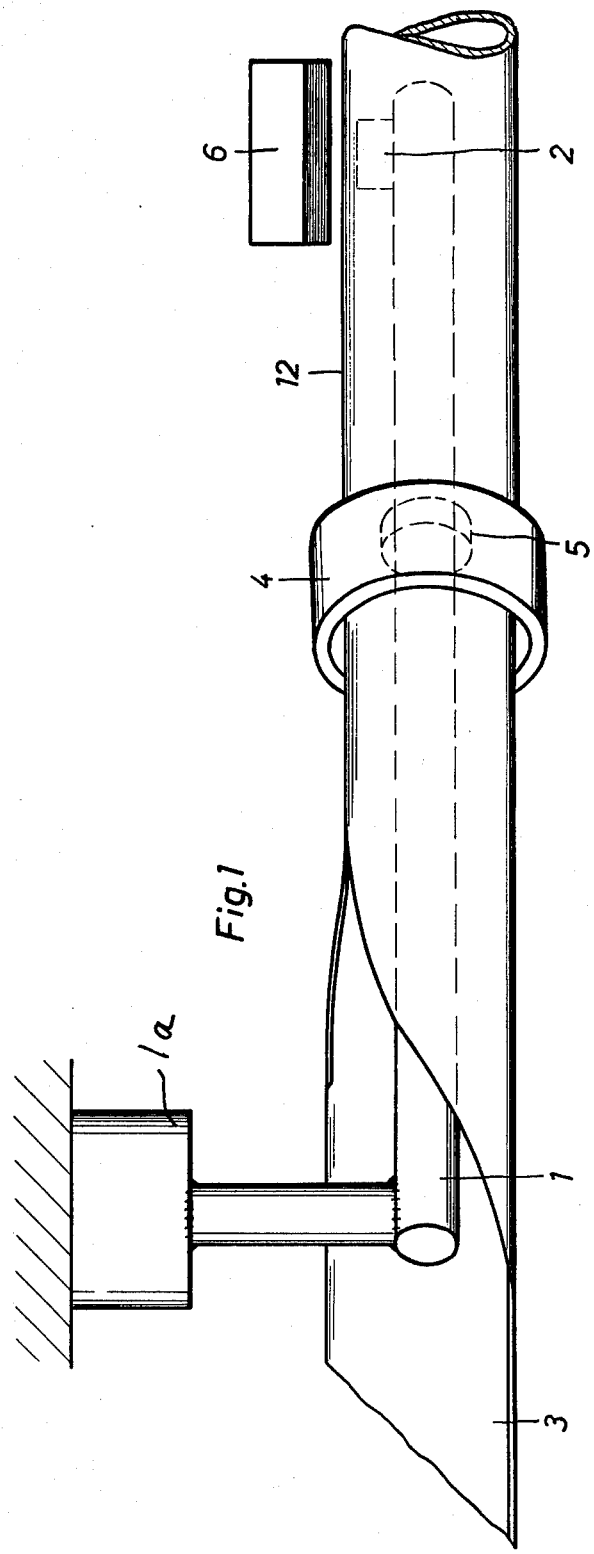

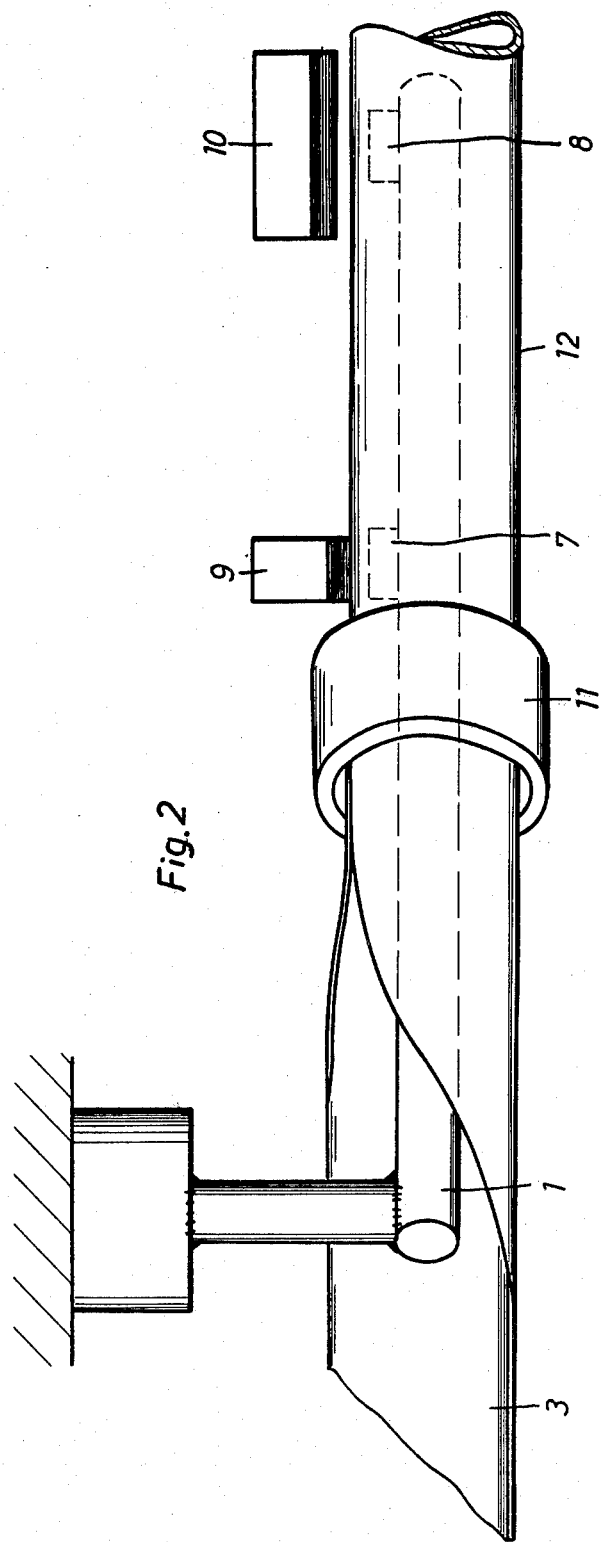

METHOD OF MAGNETICALLY TESTING TUBES DURING WELDING WHEREIN THE SAME MAGNETIC FIELD IS USED BOTH FOR HEATING AND TESTING

BACKGROUND OF THE INVENTION

The present invention relates to nondestructive continuous testing of tubes or other hollow sections having longitudinal or spiral welding seams.

Tubing, hollow sections, or other profiles are usually tested as to internal or external flaws and defects, particularly in the region of the seam. Such tests are conducted in a variety of ways; among them is the measurement of the magnetic stray flux and/or of eddy current components, etc. which are modified by any such defect. In particular, the pipes or tubes are scanned from the outside by means of magnetic probes e.g. by a.c. biased coils, and the interaction thereof with the pipe or tube material produces an output from which one extracts indications as to any flaws or absence thereof. It was found, however, that the sensitivity of this method is rather low for defects in the interior, i.e. adjacent the inner wall surface of the tube and of the seam. This drawback can be remedied either by applying a magnetic test field also along the inner surface of the tube. However, this additional step introduces an aspect of discontinuity into the process. Alternatively, the scanning field applied from the outside can be increased to such an extent that it penetrates sufficiently deep into the pipe's material and particularly into the seam. That method, however, has the drawback that actually the strong a.c. field as applied, causes the pipe's material to be heated very strongly so that a cooling step must follow. Instead of a.c. test and measuring currents, one can use d.c. to avoid parasitic heating. Flaws and defects modify also the magnetization induced by a d.c. biased coil which moves relative to the pipe. However, the pipe must be demagnetized subsequently. Moreover, the relative movement between test object and test equipment must be rather accurately controlled.

DESCRIPTION OF THE INVENTION

It is an object of the present invention to provide a new and improved method and equipment to test tubes being made by forming metal strip into a tubular configuration followed by welding the adjoining edges.

It is a particular object of the present invention to test the resulting welding seam and adjacent zones of such a tube as to defects particularly in the surface area of the seam on the inside of the tube as well as on the outside without interrupting the continuous tube forming process.

In accordance with the preferred embodiment of the invention, it is suggested to apply a magnetic field to one side of the tube, preferably the outside thereof, and to detect the interaction of that field with the material of the tube, particularly of the welding seam thereof, from the other side, preferably the inside of the tube whereby a pickup transducer is used which is introduced into the tube ahead of the location in which strip is formed into the tube, e.g. by longitudinal folding or by spiral winding. The magnetic field may be produced independently from the tube forming process; however, one may use the field as it is set up pursuant to an electric welding and/or seam annealing process. In either case, the tube and here particularly the welding seam is tested immediately following the tube making and welding. The inventive method, therefore, is based on an interaction between a test field and the tube which will be modified by a flaw irrespective of its radial location. This results in a considerably improved signal-to-noise ratio.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is a schematic view of equipment for practicing the invention, whereby particularly the measuring and testing equipment is independent from tube welding equipment; and FIG. 2 is a similar view, however, the tube welding equipment is combined with the flaw detecting equipment.

Proceeding now to the detailed description of the drawings, reference numeral 3 refers to a strip of steel, e.g. skelp which has been uncoiled and which is formed into a split tube by longitudinally folding the skelp in a manner known per se. As a result of this folding and forming process, the longitudinal edges of the skelp adjoin and are, for example, welded by means of inductive or conductive heating. Suitable rolls urge the heated edges towards each other to complete the weld.

FIG. 2 shows in particular a coil 11 and other equipment for inductively preheating the folded skelp to obtain the welding step. In addition, the welding equipment includes electrodes 9 by means of which electric current is applied to the preheated edges to complete the weld. Welding equipment is not shown in FIG. 1. Both figures show an arm 1 which extends in axial direction from the zone and location of skelp forming, into the completed tube. The arm 1 extends from a suitable stand 1a. In the past (and possibly presently as well) such an arm has been used to introduce de-scaling or de-burring equipment into the welded tube, to remove burr from the inside welding seam following completion thereof. FIG. 2 shows also a coil 10 by means of which the welding seam is annealed, using inductive heating in the process. A similar inductive heater may also be used as per FIG. 1.

In accordance with a first example of the preferred embodiment of the present invention, arm 1 is used to support a pair of measuring transducers 5, 2, of which transducer 5 is concentrically arranged to a coil 4 through which the formed and already welded tube passes. A second coil 6 is disposed longitudinally to the welding seam cooperating with the second transducer 2 which is also mounted on arm 1. Actually, only one such measuring system 4, 5 or 2, 6, is needed, but two could be used for purposes of verification.

The system 4, 5 uses an annular magnetic field producing coil 4 and a correspondingly annular pickup coil 5 by means of which an annular section of the pipe is scanned for purposes of flaw detection. The system 6, 2 uses a field which is induced by device 6 to magnetically energize the welding seam and adjacent zones only. The pickup coil 2 responds to a limited magnetization accordingly. In either case, one uses a magnetic field whose interaction with the welding seam is detected only upon complete penetration of the seam by the energizing field. This way, one obtains a rather uniform sensitivity as far as flaw detection is concerned.

The pickup coils 2 and/or 5 are connected to suitable detection circuits which respond, e.g. to signal level changes presumed to result from flaw-modified interaction of the magnetic field with the pipe material. A localized defect will introduce a temporary and rather pronounced signal peak (or drop). It was found that the inventive method yields a considerably improved signal-to-noise ratio as compared with the known methods in which field introduction and pickup is carried out from the same side. Moreover, the method is also usable (particularly the annular system 4, 5) for detecting changes in wall thickness of the pipe. These changes will produce more gradual changes in signal level and can readily be distinguished from flaw detection. A more or less local indent may actually be both, a wall thickness reduction, and a defect so that discrimination is not necessary.

It can readily be seen that the seam quality testing is carried out pursuant to the continuous production of tubing following particularly the welding step so that a running supervision of the welding process is obtained. The relationship as to timing is such that conceivably the welding process can be modified without interruption to improve welding if the testing and measuring process indicates the desirability of such an improvement. It can also be seen that this novel method is not a one-sided one and does not require insertion and retraction of measuring equipment.

The example shown in FIG. 2 is of particular advantage in that additional energy is not needed for purposes of flaw detection. Rather, flaw detection is carried out in the wake of the welding and/or annealing process, or even in direct association therewith. As stated, numeral 9 refers to an induction coil for the welding process completing the tube; conceivably, it is the only coil being used, but it could also be interpreted as a preheating device. In any event, a rather high frequency electromagnetic field is applied to the material for purposes of heating. The arm 1 carries also here a transducer 7 which responds to the magnetic field induced in the tube joined for purposes of welding. That field extends beyond the heating zone and interacts also with the just completed weld and seam. That stray field component with exhibit deviations from normal if the weld includes inhomogeneities, fissures or the like.

FIG. 2 shows also welding electrodes for conductive heating. If a.c. is used, usually at a low frequency, one will also obtain a detectable component which interacts with the just completed seam. Additionally or alternatively, a pickup coil 8 may be mounted on arm 1 adjacent to or behind the annealing coil 10. In all these cases, the electromagnetic field penetrates the welding seam and adjacent zones. Since the field is used primarily for purposes of welding, it is indeed sufficiently strong so that it not only penetrates the seam and tube material, but is so effective for some distance downstream from the welding zone proper.

The method as described is equally applicable to spirally welded tubes. In this case, the tubing usually turns on its asis as it advances longitudinally. An arm 1 can also be introduced from a location ahead of the spirally strip coiling equipment.

The invention is not limited to the embodiments described above but all changes and modifications thereof not constituting departures from the spirit and scope of the invention are intended to be included.

We claim:

1. Method of continuously, non-destructively testing tubes which are made by forming metal strip, into the tubular configuration followed by welding adjoining edges of the strip to complete the tube, comprising:

applying at least one magnetic field from one side to progressing areas of the tube by means of an electromagnetic energizing device for purposes of ac heating the edges for obtaining at least one of the following operations, welding and annealing;

detecting a result of an interaction of the heating field with the tube, and from the other side of the tube, by means of pickup transducer means; and supporting one of the transducer means and the energizing device inside of the tube by means of insertion into the tube from a point ahead of a tube forming location, the respective other one of the device and the means being located outside of the tube.

* * * * *